(12) United States Patent
Brown

(10) Patent No.: US 6,583,232 B1
(45) Date of Patent: Jun. 24, 2003

(54) BLEND OF BIORESORBABLE POLYMERS

(75) Inventor: Malcolm W. R. Brown, Leeds (GB)

(73) Assignee: Smith & Nephew PLC, London (GB)

( * ) Notice: Subject to any disclaimer, the term of this patent is extended or adjusted under 35 U.S.C. 154(b) by 0 days.

(21) Appl. No.: 09/719,857

(22) PCT Filed: Jul. 5, 1999

(86) PCT No.: PCT/GB99/02154

§ 371 (c)(1),
(2), (4) Date: Dec. 18, 2000

(87) PCT Pub. No.: WO00/01426

PCT Pub. Date: Jan. 13, 2000

(30) Foreign Application Priority Data

Jul. 7, 1998 (GB) .............................................. 9814609

(51) Int. Cl.[7] .............................................. C08G 63/91

(52) U.S. Cl. ........................ 525/410; 424/406; 424/426; 525/413; 525/415; 623/23.72; 623/23.73

(58) Field of Search ................................ 424/426, 406; 525/410, 413, 415; 623/23.72, 23.73

(56) References Cited

U.S. PATENT DOCUMENTS

| | | | | |
|---|---|---|---|---|
| 5,080,665 A | * | 1/1992 | Jarrett et al. | 606/219 |
| 5,252,642 A | * | 10/1993 | Sinclair et al. | 524/108 |
| 5,641,502 A | * | 6/1997 | Skalla et al. | 424/426 |
| 6,103,777 A | * | 8/2000 | Krishnan et al. | 523/105 |
| 6,130,271 A | * | 10/2000 | Jarrett et al. | 523/113 |
| 6,165,217 A | * | 12/2000 | Hayes | 623/11.11 |

* cited by examiner

Primary Examiner—Ana Woodward
(74) Attorney, Agent, or Firm—Larson & Taylor PLC

(57) ABSTRACT

Bioresorbable blends are presented for use in the manufacture of surgical implants. The blends comprise a bioresorbable copolymer and a further bioresorbable polymer.

15 Claims, 5 Drawing Sheets

BLEND OF BIORESORBABLE POLYMERS

The present invention relates to bioresorbable polymeric compositions for use in the manufacture of medical devices, methods of making said compositions, medical devices made from said compositions and methods of treatment of the human or animal body involving such devices.

There is a need for surgical repair devices such as sutures, bone plates, interference screws, tissue fasteners, staples and other tissue and fracture fixation devices which are bioresorbable. Reference herein to a material being "bioresorbable" means that it breaks down over a finite period of time due to the chemical/biological action of the body. Preferably, complete resorption occurs within about 5 years, More preferably within about 3 years. This breakdown is at a rate allowing the repair device to maintain sufficient integrity while the soft tissue or bone heals: surgical repair devices formed of materials which are resorbed too quickly may fail when compressive, tensile or flexural loads are placed on them before the tissue or bone has fully healed. Advantages of using bioresorbable materials over non-bioresorbable materials, e.g. metals, are that they encourage tissue repair and further surgery is not required to remove them. In addition, there is the issue of stress-shielding: tissues like bone tend to grow well in regions where there is a prevalence of high stress. If the stress is reduced or removed, because, for example, an implant is bearing all the load, then the tissue may tend to recede around it resulting in loosening over the longer term. Implanted bioresorbable materials do not tend to give rise to adverse effects due to stress-shielding.

It is known to use certain bioresorbable polymeric materials, like polyglycolic acid (PGA) and polylactic acid (PLA), for manufacturing surgical devices. These have the disadvantage, however, that they are brittle.

In addition, it is known to form blends of these materials and others, e.g. polycaprolactone (PCL), polytrimethylene carbonate (PTMC) and polydioxanone (PDO), to achieve desired physical attributes, like melting point and mechanical properties. It can prove difficult, however, to achieve the desired bioresorption rate of such materials in vivo.

Reference is also made to U.S. Pat. No. 5,475,063, which teaches a blend of a bioresorbable random copolymer and another bioresorbable polymer. This is not only the stated aim of this document, but in all the examples manufacture of the copolymer is by non-sequential addition of the components, i.e. a random copolymer will result.

It is an object of the present invention to provide polymers, particularly for medical applications, with desirable mechanical and resorption properties.

According to a first aspect of the invention, a bioresobable polymeric composition is presented comprising a blend comprising a first bioresorbable polymer and a second, bioresorbable polymer, wherein the first bioresorbable polymer is a block copolymer.

Polymer blends are usually classified as either miscible or immiscible. Many combinations of polymers form immiscible blends, this being determined by a delicate balance of entropic and enthalpic forces of the blended polymers. The compatibility of two polymers in a mobile phase depends mainly on the forces acting between the various groups in the chains of the same material as well as between the groups in the chains of the two different materials. In non-polar or weakly polar polymers the physical forces acting are principally dispersion forces. Therefore, when two non-polar polymers in a mobile isotropic liquid state are mixed together in a blend, phase separation into a dispersed and a continuous phase usually occurs. This phase separation is referred to herein as "macrophase separation".

The physical behaviour of block copolymers is related to solid state morphology. Block copolymers sometimes exhibit phase separation which typically gives rise to a continuous phase consisting of one block type in a continuous matrix consisting of a second block type. In many applications, the dispersed phase consists of hard domains which are crystalline or glassy and amorphous, the matrix being soft and rubber-like. This phase separation is referred to herein as "microphase separation". For more details regarding phase separation in block copolymers, reference is made to D. C. Allport and W. H. Janes, "Block Copolymers", Applied Science Publishers Ltd., London, 1973.

In a blend of a block copolymer and another polymer, it is possible to have microphase separation within the block copolymer itself and macrophase separation between the copolymer and the other polymer. Reference herein to microphase-separated copolymer implies that the dimensions of the domains are in the size range of less than or equal to 500 nm. Reference herein to macrophase separation implies domain sizes (i.e. domains of dispersed and continuous phases) in the size range of greater than or equal to 1 micron, unless a compatibiliser has been added, in which case the dimensions of the domains domain sizes are larger than 500 nm.

A blend of this type gives a large number of variables which may be altered, to allow the rate of bioresorption and desired mechanical properties to be precisely tailored to desired levels: not only may the second bioresorbable polymer and the at least two types of block of the first bioresorbable polymer be varied, but either polymer may form the dispersed or the continuous phase, providing even more scope for variation of the properties of the material.

As stated, the first bioresorbable polymer may form the dispersed phase or the continuous phase. Preferably, the first bioresorbable polymer forms the dispersed phase and the second bioresorbable polymer forms the continuous phase.

Advantageously, there is also microphase separation within the first bioresorbable polymer. This allows the possibility of selecting a block of the copolymer which resorbs relatively quickly, generating porosity and allowing tissue ingrowth. It also allows the possibility of having a further block of the copolymer which modifies the blend properties (e.g. toughens it).

Advantageously, the second bioresorbable polymer and each of the types of block of the first bioresorbable polymer have different resorption rates. This allows porosity to be generated by resorption in certain parts of the blend, but, at the same time, structural integrity to be maintained while this is occurring.

Most preferably, at least one of the types of block of the first bioresorbable polymer is selected to have a higher rate of resorption than both the other type(s) of block of said first bioresorbable polymer and the second bioresorbable polymer.

The first resorbable polymer is a copolymer, for example a diblock (i.e. AB), triblock (i.e. ABA) or multiblock (e.g. ABC or segmented) block copolymer.

The bioresorbable repeating units of the first bioresorbable polymer may be selected from saturated or unsaturated esters, including orthoesters, carbonates, anhydrides, amides, ethers, or saccharides.

Advantageously, the repeating units of the first bioresorbable polymer are derived from cyclic monomers capable of undergoing ring opening followed by polymerisation. Preferred cyclic monomers are cyclic esters and carbonates, like lactide (LA), glycolide (GA), caprolactone (CL), p-dioxanone (p-DO) and trimethylene carbonate (TMC). The ring opening reaction has the advantage that it may produce higher molecular weight polymers which may have superior mechanical and degradation properties. In addition, polyesters and polycarbonates have the advantage that they degrade in vivo to produce non-toxic by-products like carbon dioxide and water.

More preferably, the block copolymers comprise GA and/or TMC. Most preferably, the block copolymer is PGA-PTMC-PGA, which will also be referred to herein as Polyglyconate B and, in one form, as MAXON B™. The PGA blocks degrade relatively rapidly in vivo to give porosity and allow tissue ingrowth, while the PTMC blocks provide rubber-toughening which helps maintain the structural integrity of the blended material.

According to an advantageous embodiment of this aspect of the invention, one of the types of block of the first biodegradable polymer has a glass transition temperature, $T_g$, above ambient temperature (about 25° C.) and one has a glass transition temperature, $T_g$, below ambient temperature. Preferably, the block copolymer comprises an essentially rubber central block with a $T_g$ below ambient temperature and semi-crystalline end blocks with a $T_g$ above ambient temperature.

The first biodegradable polymer may be a linear or non-linear block copolymer or comprise linear and non-linear portions. If it is non-linear, it may be formed as a star, comb, graft, brush, hyperbranched or "hairy" block copolymer or of mixtures thereof.

The weight average molecular weight ($M_w$) of the first biodegradable polymer of the present invention may be in the range 30,000 to 3,000,000. Preferably, it is in the range 50,000 to 1,000,000.

Advantageously, the first biodegradable polymer of the present invention has an inherent viscosity of between 0.5 and 4.0 dL/g.

The second biodegradable polymer of the present invention may be a homopolymer, block or random copolymer. It may be a linear or non-linear e.g. branched, star, brush, comb, graft, hyperbranched or 'hairy' polymer or mixtures thereof.

Preferably, the second biodegradable polymer is a resorbable aliphatic polyester or polycarbonate. Again, these materials have the advantage that the decomposition products are non-toxic. More preferably, it comprises repeating units incorporating one or more of the following monomers: GA,p-DO,LA,TMC and CL. Again, these cyclic monomers polymerise by ring opening to give high molecular weight polymers with superior mechanical and degradation properties. In addition, the second polymer may comprise hydroxybutyrate (HB) monomers.

Advantageously, the second biodegradable polymer biodegrades at a lower rate than the first biodegradable polymer, i.e. the second polymer is more resistant to hydrolytic degradation and holds its strength for longer than the first biodegradable polymer. The choice of the second biodegradable polymer can therefore be determined empirically once the first polymer has been chosen.

A particularly preferred second biodegradable polymer is PLA.

A highly preferred blend according to the present invention is PGA-PTMC-PGA with PLA.

The second biodegradable polymer may make up from 1 to 99% by weight of total composition of the final product. Preferably, it makes up 20% to 90% and even more preferably, 40% to about 90% by weight of the total composition of the final product.

The bioresorbable composition according to the present invention may optionally comprise a compatibiliser, i.e. a component that is effective at the interface between the continuous and dispersed phases of the macrophase to reduce the dispersed phase domain sizes. Advantageously, the compatibiliser is a polymer, preferably an AB block copolymer. Preferred polymers comprise repeating units incorporating at least one of the following monomers: GA, DO, LA, TMC, CL. It is particularly preferred that the compatilibilser comprise at least one repeating unit present in the first polymer and at least one repeating unit present in the second polymer.

Advantageously, the compatibiliser comprises from about 1 to about 10% by weight of the total composition, preferably less than 5% wt of the total composition. It is also preferred that the compatibiliser have a weight average molecular weight ($M_W$) less than that of both the first and second polymers separately. This facilitates better interfacing of the compatibiliser between the dispersed and continuous phases. With this in mind, the compatibiliser preferably has an $M_W$ of less than 100,000, more preferably less than 50,000.

The blend of the present invention may further comprise an inorganic filler such as calcium based salts to improve the osteoconductivity of the final product. Suitable calcium-based salts include calcium carbonate in various forms, especially aragonite, calcium phosphate, calcium sulphate, hydroxyapatite, BIOGALSS™ and the material 45S5™ produced by MO-SCI Corp. The filler of the present invention may be in particle form. Preferably, the average particle size is less than 1 mm, more preferably, less than 200 microns. The blend of the present invention may comprise between about 10 to about 60% by volume of filler.

A second aspect of the invention relates to medical devices such as sutures, surgical fasteners, clips, sutures, staples, plates, screws e.g. interference screws, rods, pins and tapes, comprising the above-defined blends.

A third aspect of the invention relates to a surgical procedure comprising the step of incorporating a medical device, as defined above, into a tissue defect in a human or animal body.

A fourth aspect of the invention relates to methods of manufacture of the above-defined blends.

According to a first method, the first and second polymers are heated to form first and second polymer melts then said melts are blended. Optionally, said blend may be extruded, for example through a tapering die. The resulting blended workpiece may be subjected to one or more of the steps of granulation, drying and injection moulding to form a final product.

According to a second method, a solvent is selected in which both first and second polymers are soluble. The second polymer is added to said solvent and agitated until it is dissolved, at which point the first polymer, the block copolymer, is added to the solution and subjected to agitation. Suitably, agitation is carried out for up to one hour, preferably about 30 minutes. The solvent is then evaporated. Preferably, this is carried out in gradual stages involving one or both of natural evaporation and an evaporator, preferably a rotor evaporator. Finally, the blend is placed in a vacuum oven and heated to remove the residual solvent. Appropriate conditions for this are for a temperature of 80° C. for about 2 hours.

BRIEF DESCRIPTION OF THE DRAWINGS

Reference is made to the figures, which illustrate various aspects of the invention, as follows.

Reference is made to the following examples which illustrate various aspects of the invention. It is stressed that the invention is not limited to these examples.

EXAMPLE 1

Manufacturing Protocol

The compounding was carried out in a PRISM TSE-16-TC twin set extruder fitted with a 16 mm diameter screw having an aspect ratio of 25:1 L/D with a barrel temperature of 220° C. and a die temperature of 210° C. The feed was fed using discrete mechanical feeders and was mixed at a screw speed of 225 rpm. The extrudate was removed by a caterpillar belt and granulated using a prism microgranulator. The resulting polymer blend was dried and injection moulded to yield a suitable test bar.

EXAMPLE 1(a)

A blend of PLA (65% by weight of total blend) and MAXON B™, i.e. PGA-PTMC-PGA, (35% by weight of total blend) was made according to the above manufacturing protocol.

EXAMPLE 1(b)

A blend of PLA (35%) and PGA-PTMC-PGA (65%) was made according to the above manufacturing protocol.

EXAMPLE 1(c)

A blend of PLA (80%) and PGA-PTMC-PGA (20%) was made according to the above manufacturing protocol.

Control samples of PGA-PTMC-PGA (100%) and PLA (100%) were also produced.

EXAMPLE 1(d)

Blends of PLA/MAXON B™ were made according to the above manufacturing protocol, each blend comprising a proportion of compatibiliser (PLA-co-TMC) or (PLA-co-PGA), as detailed in Table 2, below.

Degradation Protocol

Degradation of the samples from Examples 1(a)–(d) and the controls was measured to analyse the ability of each sample to maintain its strength over a period of time. Measurement was according to the following degradation protocols: degradation of the samples at time points 0, 2 and 4 weeks from manufacture was established. Degradation was carried out as follows: samples were placed in a container of phosphate buffer solution (PBS, 100 ml), and kept in an agitating incubator at 37° C. At the relevant time, the samples were removed from the PBS, dried and tested for maximum stress according to the testing protocol described below.

Mechanical Testing Protocol

Six injection moulded samples from each of examples 1(a) to (d) were tested in a Zwick 1435 tensile testing machine with a 5 kN load cell and a test speed 50 mm/min at room temperature and using an optical extensometer to measure displacement. The sample was placed in wedge action grips and tested for maximum stress.

Results

Figure 1:
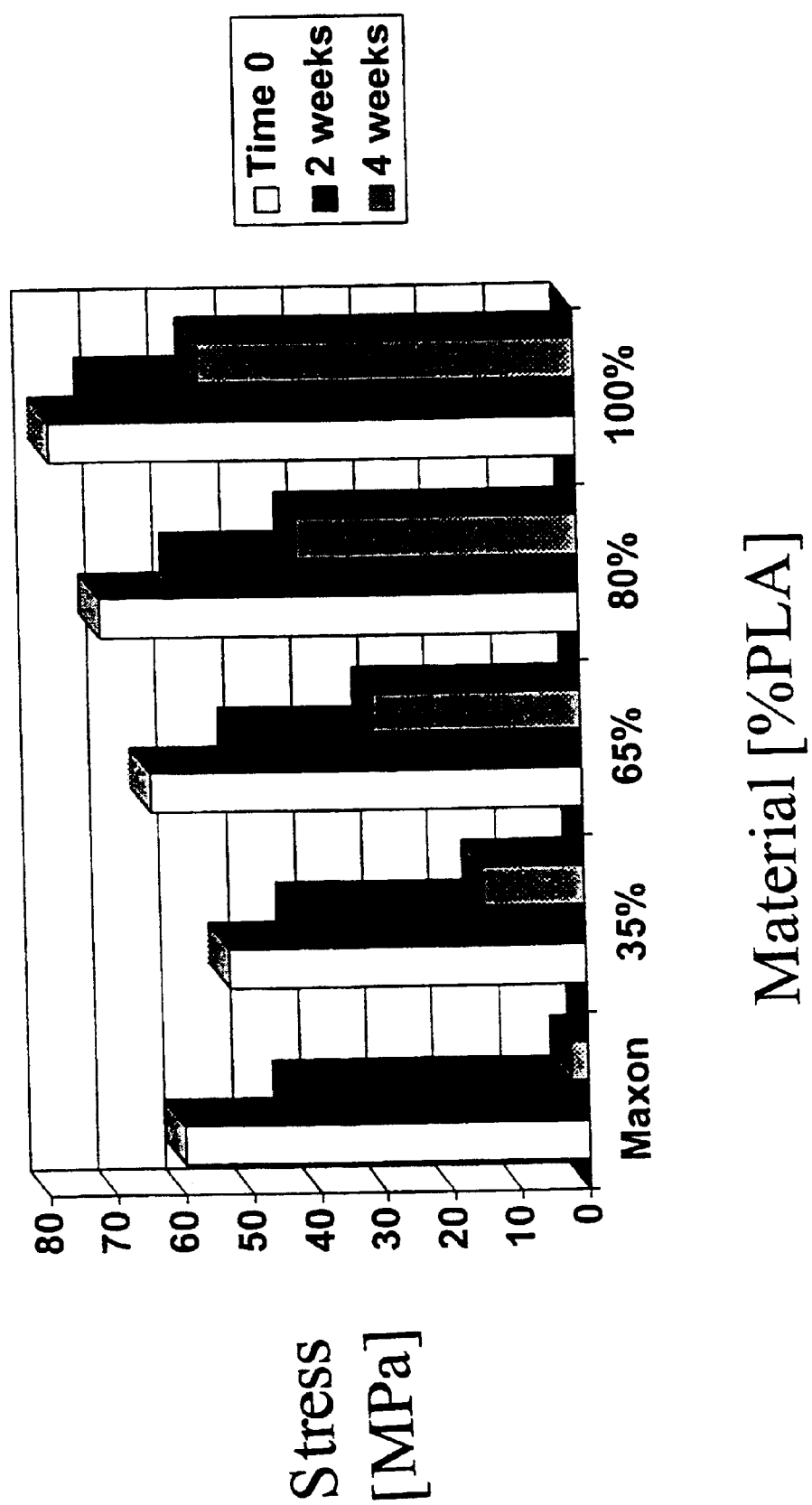
FIG. 1 illustrates in graphical form the results of Table 1, below.

Results for Examples 1(a) to (c) and the controls are presented in Table 1 and represented in FIG. 1. Results for Example 1(d) are presented in Table 2.

TABLE 1

Degradation study for PLA/Maxon B blends at time points 0, 2 and 4 weeks in PBS solution.

| Material | Stress [MPa] | | |
|---|---|---|---|
| | Time 0 | 2 weeks | 4 weeks |
| Maxon B, 100% | 60 ± 2 | 44 ± 4 | 2.5 ± 1 |
| 35:65 PLA:Maxon B | 53 ± 3 | 43 ± 1 | 15 ± 1 |
| 65:35 PLA:Maxon B | 64 ± 1 | 51 ± 1 | 31 ± 1 |
| 80:20 PLA:Maxon B | 71 ± 1 | 59 ± 1 | 42 ± 1 |
| 100% PLA | 78 ± 1 | 71 ± 2 | 56 ± 6 |

TABLE 2

Degradation study for PLA/Maxon B/Compatibiliser blends at time points 0, 2 and 4 weeks in PBS solution.

| | Stress [MPa] | | |
|---|---|---|---|
| | Time 0 | 2 weeks | 4 weeks |
| 3.5% LA-co-TMC in 31.5:65 PLA:Maxon | 54 ± 1 | 45 ± 1 | 14 ± 2 |
| 3.5% LA-co-GA in 31.5:65 PLA:Maxon | 58 ± 1 | 47 ± 1 | 14 ± 1 |
| 2% LA-co-TMC in 18:80 PLA:Maxon | 54 ± 1 | 40 ± 1 | 10 ± 1 |
| 2% LA-co-GA in 18:80 PLA:Maxon | 54 ± 3 | 37 ± 2 | 8 ± 1 |

EXAMPLE 2

Manufacturing Protocol—as for Example 1.

EXAMPLE 2(a)

A blend of PLA/MAXON B™[80% wt/20% wt] was made according to the above manufacturing protocol.

EXAMPLE 2(b)

A blend of PLA/MAXON B™[65% wt/35% wt] was made according to the above manufacturing protocol.

Degradation Protocol

Degradation of the samples from Examples 2(a) and 2(b) was measured to analyse the ability of each sample to maintain its strength over a period of time. Measurement was according to the following degradation protocols: degradation of the samples at time points 0, 2,4,8,12 and 24 weeks from manufacture was established. Degradation was carried out as follows: samples were placed in a container of phosphate buffer solution (PBS, 100 ml), and kept in an agitating incubator at 37° C. At the relevant time, the samples were removed from the PBS, dried and tested for maximum stress according to the testing protocol described below.

Mechanical Testing Protocol—as for Example 1

Results

Figure 2:
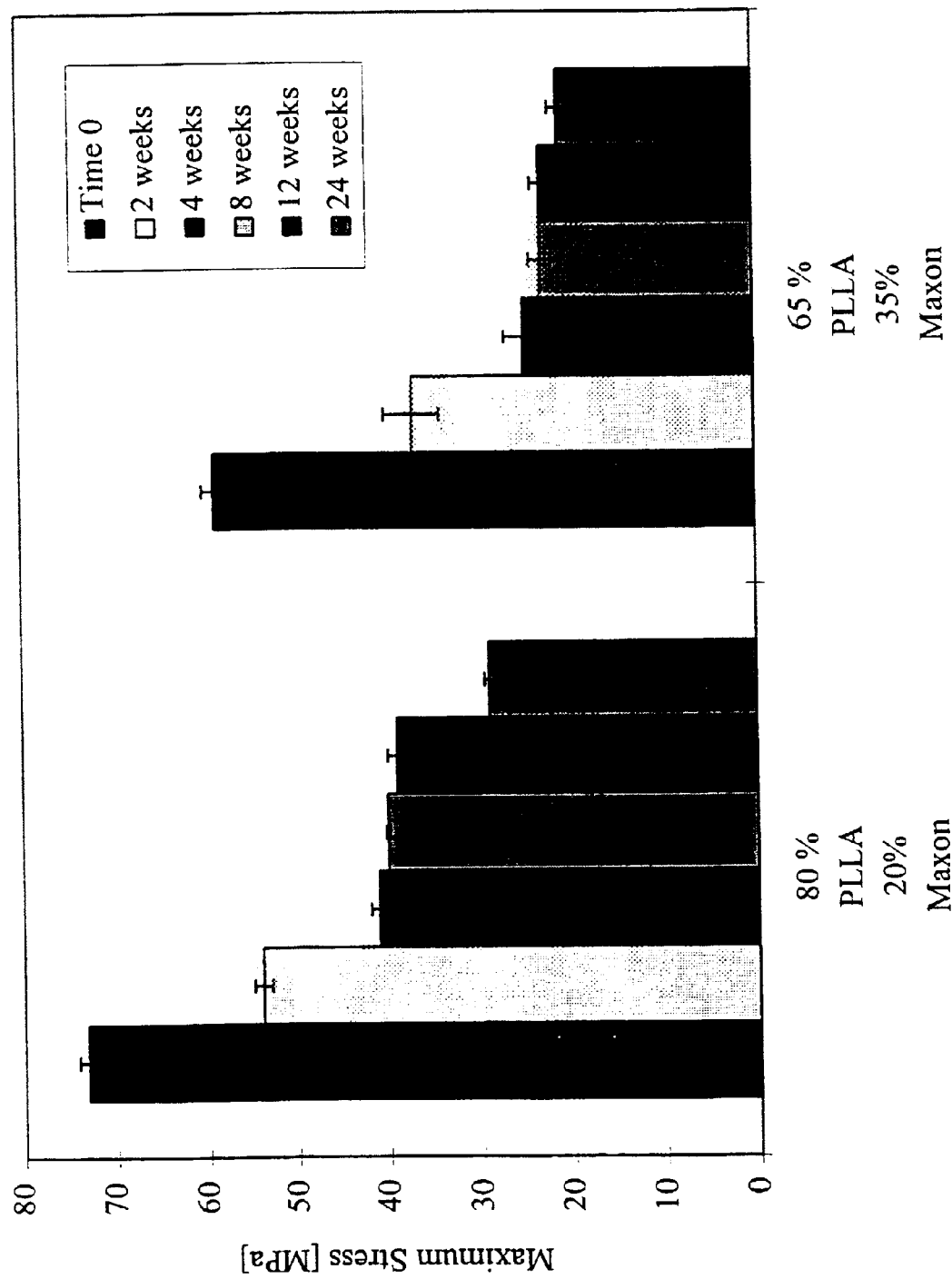
FIG. 2 illustrates in graphical form the results of Example 2, below.

For ease of presentation, the results from Examples 2(a) and 2(b) as well as the controls are presented in the form of a graph only see FIG. 2.

EXAMPLE 3

Manufacturing Protocol

The compounding was carried out in a PRISM TSE-16-TC twin set extruder fitted with a 16 mm diameter screw having an aspect ratio of 25:1 L/D. The hopper temperature and temperature of the zones was 215° C. and the die temperature was 210° C. Die pressure was 30–40 Bar. The feed was fed using discrete mechanical feeders and was mixed at a screw speed of 225 rpm. The extrudate was removed by a caterpillar belt and granulated using a prism microgranulator. The resulting polymer blend was dried and injection moulded to yield a suitable test bar.

EXAMPLE 3(a)

A blend of polycaprolactone/MAXON B™ (65%/35%) was made according to the above manufacturing protocol.

EXAMPLE 3(b)

A blend of PLA and P(ga/la-tmc-ga/la) (65%/35%) was made according to the above manufacturing protocol.

Control samples of polycaprolactone (100%) and p-PLA (100%) were also produced.

Degradation Protocol

Degradation of the samples from Examples 3(a), 3(b) and the controls was measured to analyse the ability of the sample to maintain its strength over a period of time. Measurement was according to the following degradation protocol: degradation of samples at time points 0, 4 weeks and 7 weeks from manufacture was carried out as follows. Samples were placed in a container of phosphate buffer solution (PBS, 100 ml), and kept in an agitating incubator at 37° C. At the relevant time, the samples were removed from the PBS, dried and tested for maximum stress according to the testing protocol described below.

Mechanical Testing Protocol

Four to six injection moulded samples from each of examples 1 to 4 were tested in a Zwick 1435 tensile testing machine with a 5 kN load cell and a test speed 50 mm/min at room temperature and using an optical extensometer to measure displacement. The sample was placed in wedge action grips and tested for maximum stress.

Results

Figure 3:
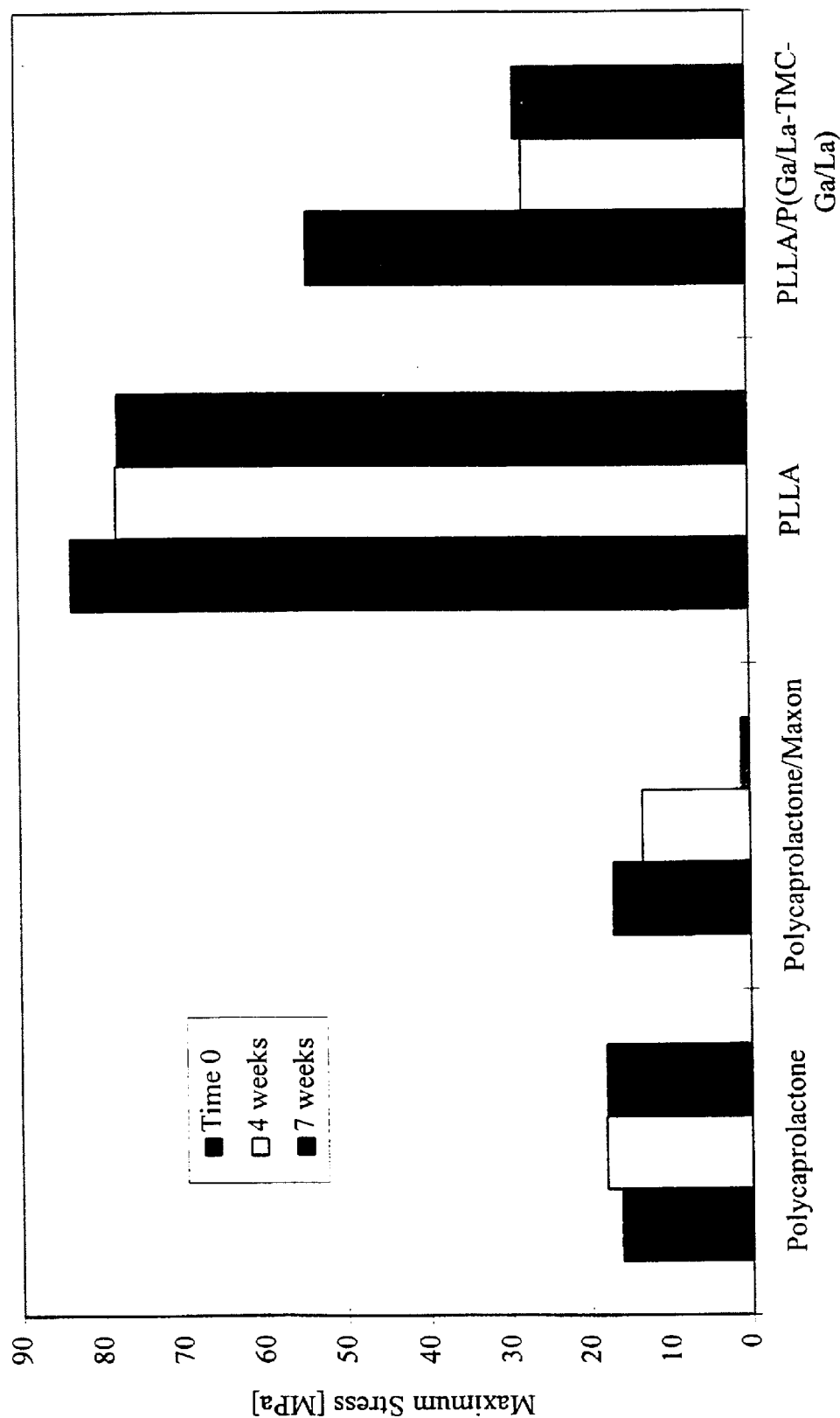
FIG. 3 illustrates in graphical form the results of Table 3, below.

The results from Examples 3(a) and 3(b) as well as the controls are presented in Table 3 and represented in FIG. 3.

TABLE 3

Degradation study for PCL/Maxon B and PLA/P(GA/LA-TMC-GA/LA) blends at time points 0, 2 and 7 weeks in PBS solution.

| Material | Maximum Stress [MPa] | | |
| --- | --- | --- | --- |
| | Time 0 | 4 weeks | 7 weeks |
| Polycaprolactone (PCL) | 16 ± 2 | 18 ± 1 | 18 ± 1 |
| PCL/MAXON B | 17.1 ± 0.5 | 13.4 ± 1 | 1 ± 2 |
| PLA | 83.6 ± 0.3 | 78 ± 2 | 77.8 ± 1.2 |
| PLA/P(GA/LA-TMC-GA/LA) | 54 ± 5 | 27.9 ± 1.1 | 28.9 ± 0.7 |

EXAMPLE 4

Manufacturing Protocol

Samples of (a) Polyglyconate B (i.e. PGA-PTMC-PGA), (b) p-PLA and (c) a Polyglyconate B/p-PLA blend in the weight ratio 40:60 were produced according to the protocol described in Example 1.

Degradation Protocol

The above materials were subjected to degradation for 10 weeks at pH 7 and 37° C. followed by further degradation for 4 weeks at pH 3 and 50° C.

Results

Figure 4:
FIG. 4 is a x1500 TEM photograph of the surface of a tensile fracture surface of a sample of polyglyconate B after a 10 week degradation, as described in the Degradation Protocol of Example 4, below.
Figure 5:
FIG. 5 is a x1500 TEM photograph of the surface of a tensile fracture surface of a sample of p-PLA after a 10 week degradation, as described in the Degradation Protocol of Example 4, below.
Figure 6:
FIG. 6 is a x1500 TEM photograph of the surface of a tensile fracture surface of a sample of a polyglyconate B/p-PLA blend in the ratio 40:60 after a 10 week degradation, as described in the Degradation Protocol of Example 4, below.

Preliminary transmission electron microscopy (TEM) analysis was carried out on degraded blend tensile fracture samples (a), (b) and (c). With reference to FIGS. 4–6, it was found that PLA (see FIG. 4) and polyglyconate B (see FIG. 5) were still composed of a single phase, while the blend had developed a honeycomb structure (see FIG. 6).

From the maximum stress data gained in relation to the single second polymers, PLA and PCL—see FIGS. 1 and 3—it is evident that bioresorption, as measured in terms of maximum stress, is occurring slowly. FIG. 1 also illustrates that particularly PLA on its own has a high maximum stress, so is capable of providing the high strength required in certain implants. Polycaprolactone has a lower strength, illustrating that it is possible to tailor such properties to the requirements at hand.

Considering the blends, it is apparent that the rate of bioresorption of the second polymer can be significantly modified by addition of the first polymer, the block copolymer. With reference to FIG. 1, it is evident that the rate of degradation can be increased by increasing the proportion of MAXON B™ in the blend. With reference to FIG. 3, it is evident that the same effect can also be achieved by adding MAXON B™ to polycaprolactone. Comparing the results for polycaprolactone/MAXON B™(65/35) with those of PLA/MAXON B™(65/35), it can be seen that a lower initial strength for polycaprolactone/MAXON B™(65/35) is offset by a high rate of resorption, again showing that it is possible to tailor materials to achieve a balance of strength and rate of bioresorption.

The same sort of effects achieved by adding MAXON B™ to the second polymer are also achieved by blending in other block copolymers, as can be seen from FIG. 3.

With reference to Table 2 and comparing the first two materials with the result from Table 1 relating to PLA/MAXON B™ (35/65), there is some indication of a slightly faster degradation rate, although this particular comparison is not very conclusive. In fact, other results have indicated that use of the compatibiliser can increase the degradation rate of the blend. While not wishing to be bound by any theory, this is believed to be due to the increased surface area of contact between the dispersed and continuous phases (in the macrophase separated dispersion), due to the smaller domain sizes of the dispersed phase, resulting from use of the compatibiliser.

With reference to FIG. 2, degradation of the blend over the longer term is illustrated. The plateau-like region derives from the fact that the MAXON™ has mostly been degraded at this point leaving a porous honeycomb of PLA which itself degrades slowly over the ensuing weeks and months.

This honeycomb structure is illustrated in FIG. 6. The porosity of the blend is due to the higher degradation rate of the PGA blocks in the polyglyconate B. The pore size was found to be dependent upon the blend ratio. For a Polyglyconate B/PLA blend in the ratio 40:60 pores in the 5–10 micron size-range were generated.

Although, as illustrated in FIGS. 1, 3 and 4, PLA on its own has a relatively slow rate of hydrolytic degradation, this material is found to degrade more rapidly when blended with a copolymer according to the invention, i.e. in situation like that illustrated in FIGS. 1 and 2, because of the increased surface area for degradation resulting from the honeycomb structure (FIG. 6) remaining after degradation of the copolymer.

Figure 7:
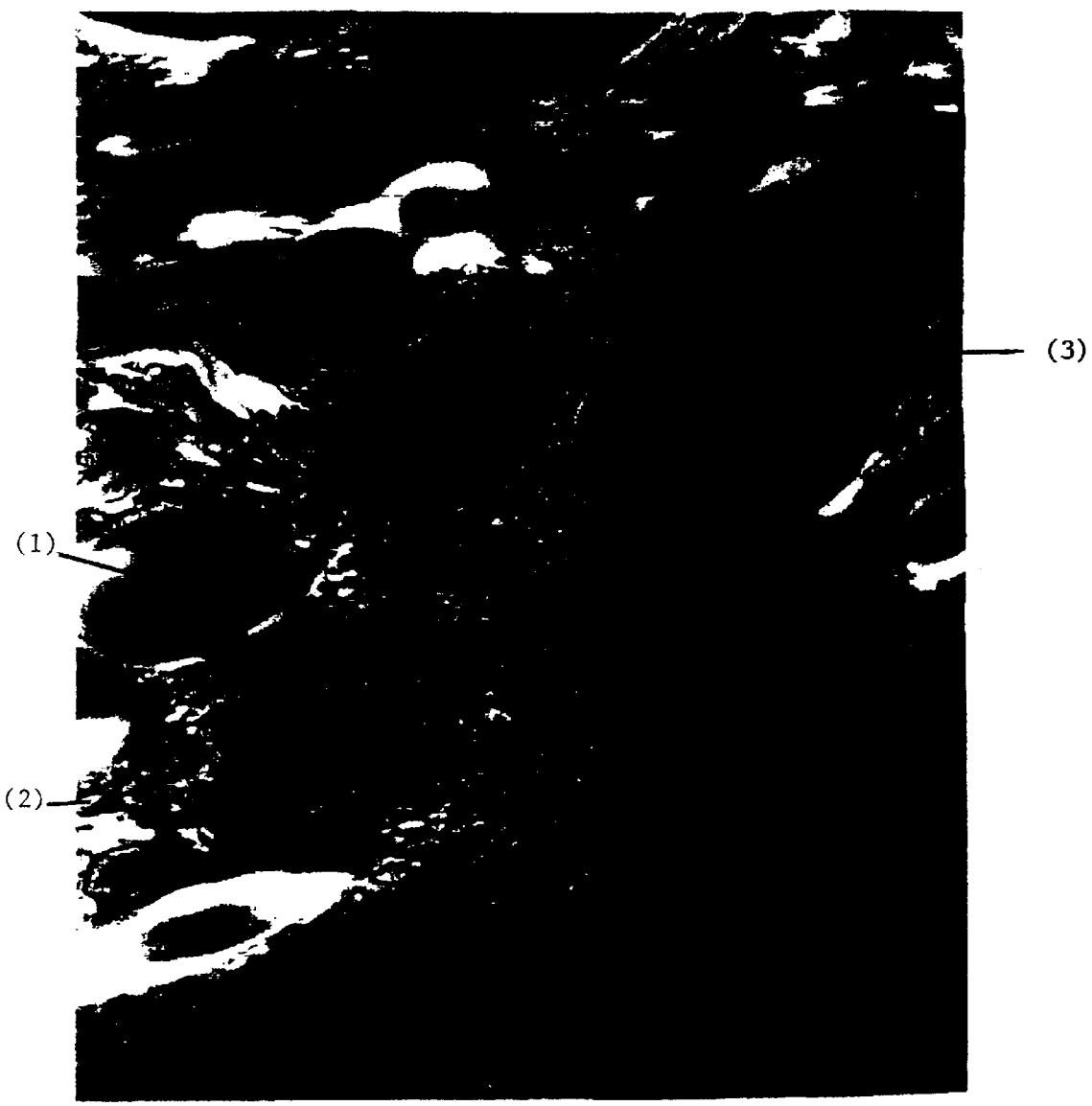
FIG. 7 is a x8000 SEM image of a PLA/Polyglyconate B (MAXON B™) blend comprising 20% wt. PLA and 80% wt. Polyglyconate B.

Lastly, reference is made to FIG. 7. This SEM image illustrates islands of dispersed phase (1), PLA in this case, in a continuous phase of Polyglyconate B (i.e. PGA-PTMC-PGA or MAXON B™). It can clearly be seen that the continuous phase is, in fact, not a single phase but is also a dispersion due to the microphase separation. In this instance, light areas of semicrystalline PGA (2) are interspersed with dark areas of rubber-like PTMC (3). Although blends, as illustrated in this figure do fall under the scope of the invention, the preferred blends according to the present application are those in which the block copolymer forms the dispersed phase.

What is claimed is:

1. Bioresorbable polymeric composition comprising a blend comprising a first bioresorbable polymer and a second bioresorbable polymer, wherein the first bioresorbable polymer is a block copolymer wherein the copolymer blocks comprise polyglycolic acid and wherein the second bioresorbable polymer and each of the types of block of the first bioresorbable polymer all have different resorption rates, and wherein there is microphase separation within the first bioresorbable polymer and macrophase separation between the first and second bioresorbable polymers.

2. Bioresorbable composition according to claim 1, wherein the blocks of the first bioresorbable polymer are saturated or unsaturated esters, orthoesters, carbonates, anhydrides, ethers, amides or saccharides.

3. Bioresorbable composition according to claim 1, wherein the blocks of the first bioresorbable polymer are polyesters or polycarbonates.

4. Bioresorbable composition according to claim 1, wherein the blocks of the first bioresorbable polymer are derived from cyclic monomers selected from the group comprising glycolide, dioxanone, lactide, trimethylene carbonate and caprolactone.

5. Bioresorbable composition according to claim 1, wherein the copolymer blocks comprise polytrimethylene carbonate.

6. Bioresorbable composition according to claim 1, wherein the first bioresorbable polymer is PGA-PTMC-PGA.

7. Bioresorbable composition according to claim 1, wherein the second bioresorbable polymer comprises a homopolymer, a block copolymer or a random copolymer.

8. Bioresorbable composition according to claim 1, wherein the second bioresorbable polymer comprises a bioresorbable aliphatic polyester or polycarbonate.

9. Bioresorbable composition according to claim 1, wherein the second bioresorbable polymer is derived from cyclic monomers selected from the group comprising dioxanone, lactide, trimethylene carbonate, caprolactone.

10. Bioresorbable composition according to claim 1, wherein the second bioresorbable polymer is polylactic acid.

11. Bioresorbable composition according to claim 1, wherein the first bioresorbable polymer forms the dispersed phase and the second bioresorbable polymer forms the continuous phase.

12. Bioresorbable composition according to claim 1, wherein one of the types of block of the first bioresorbable polymer is selected to have a higher rate of resorption than both the other type(s) of block of said first bioresorbable polymer and the second bioresorbable polymer.

13. Medical device comprising a bioresorbable composition according to claim 1.

14. Surgical procedure comprising the step of incorporating the medical device of claim 13 into a tissue defect in a human or animal body.

15. Method of manufacture of the bioresorbable composition of claim 1, comprising the steps of heating the first and second polymers to form first and second polymer melts and blending said melts.

* * * * *